(12) United States Patent
Rahbaran et al.

(10) Patent No.: US 11,083,817 B2
(45) Date of Patent: Aug. 10, 2021

(54) HYGIENE PRODUCT

(71) Applicant: LENZING AG, Lenzing (AT)

(72) Inventors: Shayda Rahbaran, Vöcklabruck (AT); Bianca Schachtner, Vöcklabruck (AT)

(73) Assignee: Lenzing Aktiengesellschaft, Lenzing (AT)

( * ) Notice: Subject to any disclaimer, the term of this patent is extended or adjusted under 35 U.S.C. 154(b) by 1389 days.

(21) Appl. No.: 14/381,029

(22) PCT Filed: Feb. 22, 2013

(86) PCT No.: PCT/AT2013/000033
§ 371 (c)(1),
(2) Date: Aug. 26, 2014

(87) PCT Pub. No.: WO2013/126934
PCT Pub. Date: Sep. 6, 2013

(65) Prior Publication Data
US 2015/0044926 A1 Feb. 12, 2015

(30) Foreign Application Priority Data
Feb. 28, 2012 (AT) .................. A 253/2012

(51) Int. Cl.
*A61L 15/28* (2006.01)
*A61F 13/511* (2006.01)
*D04H 1/52* (2006.01)
*A61L 15/62* (2006.01)
*A61F 13/513* (2006.01)
*D04H 1/26* (2012.01)
*D04H 1/492* (2012.01)
*D04H 1/732* (2012.01)
*D04H 1/541* (2012.01)
*A61F 13/15* (2006.01)
*A61L 15/52* (2006.01)
*D04H 1/425* (2012.01)

(52) U.S. Cl.
CPC .............. *A61L 15/28* (2013.01); *A61F 13/15* (2013.01); *A61F 13/513* (2013.01); *A61F 13/51113* (2013.01); *A61F 13/51121* (2013.01); *A61L 15/52* (2013.01); *A61L 15/62* (2013.01); *D04H 1/26* (2013.01); *D04H 1/425* (2013.01); *D04H 1/492* (2013.01); *D04H 1/52* (2013.01); *D04H 1/541* (2013.01); *D04H 1/732* (2013.01); *Y10T 442/2484* (2015.04); *Y10T 442/603* (2015.04); *Y10T 442/611* (2015.04); *Y10T 442/637* (2015.04); *Y10T 442/659* (2015.04); *Y10T 442/668* (2015.04); *Y10T 442/68* (2015.04); *Y10T 442/681* (2015.04); *Y10T 442/682* (2015.04); *Y10T 442/689* (2015.04); *Y10T 442/696* (2015.04)

(58) Field of Classification Search
CPC .......... A61L 15/28; A61L 15/52; A61L 15/62; C08L 1/00; C08L 13/15; C08L 13/51113; C08L 13/51121; D04H 1/26; D04H 1/425; D04H 1/492; D04H 1/52; D04H 1/541; D04H 1/732; Y10T 442/2484; Y10T 442/603; Y10T 442/611; Y10T 442/637; Y10T 442/659; Y10T 442/668; Y10T 442/68; Y10T 442/681; Y10T 442/682; Y10T 442/689
See application file for complete search history.

(56) References Cited

U.S. PATENT DOCUMENTS

| | | | |
|---|---|---|---|
| 2,231,890 A | 2/1941 | Esselmann et al. | |
| 2,234,734 A | 3/1941 | Kline | |
| 2,902,391 A | 9/1959 | Daul et al. | |
| 2,903,382 A | 9/1959 | Berls | |
| 3,232,823 A | 2/1966 | Soblev | |
| 3,347,968 A | 10/1967 | Rainer et al. | |
| 3,408,291 A | 10/1968 | Thomas et al. | |
| 4,770,925 A * | 9/1988 | Uchikawa | D04H 1/54 428/219 |
| 5,008,385 A | 4/1991 | Diamantoglou | |
| 5,163,931 A | 11/1992 | Aldrett | |
| 5,273,596 A * | 12/1993 | Newkirk | A61F 13/51121 156/290 |
| 5,968,855 A * | 10/1999 | Perdelwitz, Jr. | A61F 13/53747 264/103 |

(Continued)

FOREIGN PATENT DOCUMENTS

| | | |
|---|---|---|
| CH | 213876 A | 3/1941 |
| CH | 359832 A | 1/1962 |

(Continued)

OTHER PUBLICATIONS https://patents.google.com/patent/JP2004073759A/en?oq=JP+2015507977+A (Year: 2004).*

(Continued)

*Primary Examiner* — Arti Singh-Pandey
(74) *Attorney, Agent, or Firm* — Venable LLP

(57) ABSTRACT

The invention concerns a hygiene product comprising at least one layer of a nonwoven wherein the nonwoven layer comprises man-made cellulosic fibers wherein the layer or the layers has or have a rewet value of equal to or less than 30% and a liquid strike through time of equal to or less than 6 seconds for the use in disposable hygiene products, such as diapers, feminine pads and incontinence products or in wet wipes like toilet wipes, facial wipes, cosmetic wipes, baby wipes and sanitary wipes for cleaning and disinfection.

22 Claims, No Drawings

(56) References Cited

U.S. PATENT DOCUMENTS

| | | | |
|---|---|---|---|
| 6,342,268 | B1 | 1/2002 | Samain |
| 6,372,035 | B1 | 4/2002 | Juppo et al. |
| 2003/0092804 | A1 | 5/2003 | Detering et al. |
| 2004/0259445 | A1 | 12/2004 | Hilfenhaus et al. |
| 2005/0176326 | A1 | 8/2005 | Bond et al. |
| 2005/0245159 | A1* | 11/2005 | Chmielewski .... A61F 13/51458 442/268 |
| 2006/0060814 | A1 | 3/2006 | Pawlowska et al. |
| 2007/0026228 | A1 | 2/2007 | Hartmann et al. |
| 2007/0118087 | A1* | 5/2007 | Flohr ................ A61F 13/5376 604/372 |
| 2007/0219517 | A1 | 9/2007 | Rosenfeld et al. |
| 2008/0146792 | A1 | 6/2008 | Wang et al. |
| 2009/0131909 | A1 | 5/2009 | Bjornberg et al. |
| 2011/0021098 | A1 | 1/2011 | Tabellion et al. |
| 2011/0045078 | A1 | 2/2011 | Kolbe et al. |
| 2013/0236647 | A1 | 9/2013 | Samain et al. |
| 2014/0315461 | A1* | 10/2014 | Schachtner ........... D06M 13/13 442/327 |
| 2015/0329707 | A1* | 11/2015 | Roggenstein ............ D01F 2/10 442/327 |

FOREIGN PATENT DOCUMENTS

| | | | |
|---|---|---|---|
| DE | 1222204 | B | 8/1966 |
| DE | 1468539 | A1 | 12/1968 |
| DE | 1469448 | A1 | 3/1969 |
| DE | 3317724 | A1 | 11/1983 |
| DE | 3920356 | A1 | 12/1989 |
| DE | 69801056 | T2 | 11/2002 |
| DE | 102006053326 | A1 | 5/2008 |
| DE | 10200754702 | A1 | 5/2009 |
| EP | 0228576 | A1 | 7/1987 |
| EP | 0353212 | A1 | 1/1990 |
| EP | 0947549 | A1 | 10/1999 |
| FR | 707688 | A | 7/1931 |
| FR | 2767270 | A1 | 2/1999 |
| GB | 343104 | | 2/1931 |
| GB | 477029 | A | 12/1937 |
| GB | 586549 | A | 3/1947 |
| GB | 780967 | A | 8/1957 |
| GB | 887466 | A | 1/1962 |
| GB | 1042182 | A | 9/1966 |
| GB | 2121069 | A | 12/1983 |
| GB | 2126260 | A | 3/1984 |
| GB | 2221928 | A | 2/1990 |
| GB | 2252984 | A | 8/1992 |
| JP | S54-102095 | A | 8/1979 |
| JP | H01-158953 | A | 6/1989 |
| JP | 2004-073759 | A | 3/2004 |
| JP | 2004-344443 | A | 12/2004 |
| JP | 2006307402 | A | 11/2006 |
| JP | 2009-000173 | A | 1/2009 |
| JP | 2010106251 | A | 5/2010 |
| JP | 2011-135979 | A | 7/2011 |
| WO | 9908724 | A2 | 2/1999 |
| WO | 9937859 | A1 | 7/1999 |
| WO | 0163036 | A1 | 8/2001 |
| WO | 2004024044 | A1 | 3/2004 |
| WO | 2012066015 | A1 | 5/2012 |
| WO | 2013/067556 | A1 | 5/2013 |

OTHER PUBLICATIONS

Deanin, Rudolph D., et al. "Breathable, Permanent Water-Repellent Treatment of Cotton 1", textile Research Journal, Nov. 1970, vol. 40, No. 11, pp. 970-974.

R. Adams, "Organic Reactions vol. III," John Wiley & Sons Inc. NY, p. 146 (1946).

J.C. Sauer, "Ketene Dimers from Acid Halides," Journal of the American Chemical Society, vol. 69, pp. 2444-2448 (1947).

H. Zhang, "The Role of Vapour Deposition in the Hydrophobization Treatment of Cellulose Fibres using Alkyl Ketene Dimers and Alkenyl Succinc Acid Anhydrides," Colloids and Surfaces A: Physiochem. Eng. Aspects, vol. 297, pp. 203-210 (2007).

Collier, B. J., et al. "Understanding Textiles" Prentice-Hall, 6th Ed., p. 492 (2001).

Incorporated, Define Incorporated at Dictionary.com, http://www.dictionary.com/browse/incorporated, retrieved Feb. 14, 2017.

Notification of Transmittal of Translation of the International Preliminary Report on Patentability and Written Opinion issued in International Application No. PCT/EP2013/075580 dated Jun. 25, 2015—6 pages.

K. Brederck and F. Hermanutz, "Man-made cellulosics," Rev. Prog. Color, 35, pp. 59-75 (2005).

\* cited by examiner

HYGIENE PRODUCT

BACKGROUND OF THE INVENTION

Field of the Invention

The present invention concerns a hygiene product, especially for the use in wet wipes and in the form of topsheets and acquisition/distribution layers in disposable absorbent hygiene products, like feminine protection pads, incontinence products and baby diapers.

Wet wipes are absorbent nonwoven fabrics with lotion for cleaning or disinfection of the skin or surfaces. These products are like toilet wipes, facial wipes, cosmetic wipes, baby wipes and sanitary wipes.

Absorbent hygiene products may be structured with a topsheet, an acquisition/distribution layer, an absorbent core and a back sheet. These are sandwich structures with an absorbent core, often comprising a blend of fiberized fluff pulp and superabsorbent polymer (SAP).

The topsheet is usually a layer of mainly polyester (PET) or polypropylene (PP) nonwovens or can be a blend of both materials. The Acquisition/distribution layer is mainly made of fluff pulp and bicomponent fibers manufactured by airlaid technology and through air bonding. It is designed to distribute and transfer the liquid from the topsheet to the absorbent core to reduce skin wetness and enhance absorbency in the absorbent core. The back sheet is usually formed of a polyethylene (PE) film or alternatively of a nonwoven/film composite which may be breathable. It prevents wetness transfer to the clothes. The product is fastened to the underwear by an adhesive strip on the back sheet which is protected by release paper prior to use. The product is designed to provide comfort, skin protection and reduced odor.

According to EDANA, absorbent hygiene products such as baby diapers, incontinence products and feminine protection pads have all become essential features of modern day life. Good skin health and hygiene affects wellbeing, the ability to function and comfort. Over the last twenty years absorbent hygiene products have contributed to improved skin health and hygiene through the use of innovative topsheet materials which fluids quickly penetrate to lower layers with a resulting reduction in skin wetness.

Current topsheets used in absorbent hygiene products are mainly made of synthetic materials such as polypropylene (PP) spunbond, polyester (PET) and bicomponent fibers to achieve low liquid strike through time (inlet time) and low rewet value which reduces skin wetness.

The acquisition/distribution layer is mainly made of fluff pulp and bicomponent fibers manufactured by airlaid technology and through air bonding.

Due to ecological reasons cellulosic fibers, especially man-made cellulosic fibers, continue to gain importance and there is a demand for nonwoven fabrics made from cellulosic fibers which show low liquid strike through time, low rewet value and improved liquid management in absorbent hygiene products.

In US 2009/0131909 it is mentioned that cellulosic fibers treated with hydrophobic agents are suited for the manufacturing of topsheets. The document is silent about the rewet and liquid strike through performance of topsheets, especially made from man-made cellulosic fibers.

The objective of the invention is to provide a hygiene product which allows the liquid to strike through quickly without making the surface of the hygiene products wet which helps to maintain good skin health (dry feeling).

The inventive hygiene product comprises at least one layer of a nonwoven wherein the nonwoven layer comprises man-made cellulosic fibers, wherein the layer or the layers has or have a rewet value of equal to or less than 30% and a liquid strike through time of equal to or less than 6 seconds.

A single layer nonwoven solely made from hydrophobic man-made cellulosic fibers with a low content of hydrophobic agent shows low inlet time, but increases the rewet value.

Surprisingly it has been found that the addition of wetting agents to the layer with a high content of hydrophobic agent improves the liquid strike through (inlet time) performance. The wetting agent lowers the surface tension of the hydrophobic fibers in the layer, which allows the layer to wet out and the fluid to pass through. Such one layer nonwoven products are especially suited for topsheets and wet wipes.

A hygiene product consisting of one layer of a nonwoven fabric, which nonwoven fabric comprises a blend of man-made cellulosic fibers and hydrophobic man-made cellulosic fibers and which nonwoven is treated with a wetting agent shows a low inlet time.

Preferably the hygiene product comprises a blend of 75 to 90% by mass of hydrophobic man-made cellulosic fibers and 25 to 10% by mass of man-made cellulosic fibers provided that the total amount of the nonwoven fabric is 100% by mass.

The nonwoven for the single layer or the first layer is preferably apertured.

Man-made cellulosic fibers are inherently hydrophilic. To produce hydrophobic man-made cellulosic fibers the normal fibers are treated with a hydrophobic agent. The preferred hydrophobic agent is an Alkyl Ketene Dimere (AKD), the hydrophobic fibers contains the hydrophobic agent in an amount of 0.005 to 0.5% per mass, preferably of 0.01 to 0.1% per mass. Other suitable hydrophobic agents are DACC (di-alkyl-carbamoyl-chloride) or stearic acid amides such as Leristan HE I/42 from the company Zschimmer & Schwarz.

The invention is shown by the following examples.

Test Methods

Inlet Time

The inlet time test is a modified version of the method outlined in US 2007/0219517 of Johnson & Johnson:

A sample of top sheet was cut and clamped onto an absorbent core. The absorbent core used is a typical liquid-absorbent material commonly used in disposable absorbent products. The absorbing material of the core used in this invention comprises hydrophilic fibers such as cellulose fibers (fluff pulp, rayon) and superabsorbent products such as sodium acrylate-acrylic-acid polymers.

The test liquid is a mixture of 49.50% of 0.9% (w/w) Sodium Chloride solution, and 49.05% Glycerin, 1.00% Phenoxyethanol and 0.45% Sodium Chloride.

A small amount of blue tint was also added to the test liquid in order to make it easier to observe the liquid distribution during testing. 4.0 ml of test liquid was pipetted onto the top sheet from a height of 3 cm. The time was recorded from the initial release of the liquid to the moment all the liquid passed through or into the top sheet. The time to pipette the 4.0 ml of liquid was approximately 3.6 seconds.

Rewet Weight

The main rewet test used in the evaluation was a modified version of the method outlined in US 2007/0219517:

Stacks of ten 7 cm diameter Whatman 41 filter papers were weighed and placed centered on the test area of the inlet test, 5 minutes (±10 s) after completion of the inlet time test. A pressure of 4.14 kPa was placed on the filter papers for 5 minutes (±10 s). The filter papers were then removed and reweighed to calculate the rewet value.

Manufacturing of Nonwoven Fabrics for Topsheets

Parallel-laid webs were carded and hydroentangled, The mean fabric weight is 30 g/m². All fabrics were hydroentangled on a medium aperture size belt with ca. 14% open area and a mean aperture size of approx. 2.4 mm²

EXAMPLE 1 (Comparison)

30 g/m² carded, hydroentangled and apertured (medium mesh size) nonwoven fabrics were manufactured from 1.7 dtex dull hydrophobic viscose at different levels of the hydrophobic agent AKD 452 N (AKD 452 N is an alkyl-ketene-dimere-formulation commercially available from the company Kemira). Blends of the hydrophobic viscose with man-made cellulosic fibers were also tested. The inlet time and rewet values of the topsheets were tested according to the test methods described above.

Table 1 shows that viscose fibers with a low concentration of hydrophobic treatment (sample 1.3, 1.4) have inlet time about the same value as the reference polyester (sample 1.1), but the rewet value is higher than desired for this application. With a higher concentration of the hydrophobic agent on the fiber, the inlet time is out of the range (sample 1.5). Also out of the range are the blends of hydrophobic man-made cellulosic fibers with man-made cellulosic fibers where the proportion of the hydrophobic man-made cellulosic fibers is higher than 25% (sample 1.6 and 1.7). A blend of 25% hydrophobic man-made cellulosic fibers with man-made cellulosic fibers shows a sufficient performance (sample 1.8).

TABLE 1

| Sample | Apertured nonwoven fabrics | Inlet time (s) | Rewet (%) |
|---|---|---|---|
| 1.1 | Polyester (PET) (comparison) | 4.0 | 7 |
| 1.2 | Viscose (comparison) | 5.0 | 64 |
| 1.3 | Hydrophobic viscose at 0.005% AKD | 4.4 | 51 |
| 1.4 | 90% Hydrophobic viscose at 0.01% AKD + 10% Tencel | 4.8 | 47 |
| 1.5 | Hydrophobic viscose at 0.05% AKD | >20 | Not determinable |
| 1.6 | 75% hydrophobic viscose at 0.1% AKD + 25% viscose | >60 | Not determinable |
| 1.7 | 75% hydrophobic viscose at 0.1% AKD + 25% Tencel | >60 | Not determinable |
| 1.8 | 25% hydrophobic viscose at 0.1% AKD + 75% Tencel | 6 | 30 |

EXAMPLE 2

To improve the wettability of the hydrophobic fabrics and reduce the inlet time and rewet value, nonwoven fabrics made of hydrophobic viscose 1.7 dtex dull at 0.1% AKD 452N were additionally treated with a wetting agent (Plantacare 810 UP) from the company BASF. A 1.0% solution of the wetting agent "Plantacare 810 UP" (50% active substance) was made with distilled water and the pH was corrected to 5 with 30% citric acid solution. This solution was applied using a fine mist compressed air spray onto the upper surface of certain topsheets to a level of 1% active wetting agent by weight of topsheet. The samples were allowed to dry under ambient conditions overnight before testing. Inlet time and rewet values were tested on each fabric according to the test methods described above.

It can be seen that nonwoven fabrics from blends of 75% hydrophobic viscose at 0.1% AKD 452N with 25% viscose fibers (sample 1.6) or with 25% Tencel fibers (sample 1.7) with an additional treatment of 1% of the wetting agent "Plantacare 810 UP" have significantly reduced the inlet time of the topsheets and the rewet values (samples 2.1 and 2.2).

TABLE 2

| Sample | Composition | Inlet time (sec) | Rewet (%) |
|---|---|---|---|
| 2.1 | 75% hydrophobic viscose at 0.1% AKD + 25% viscose + wetting agent | 4.9 | 30 |
| 2.2 | 75% hydrophobic viscose at 0.1% AKD + 25% Tencel + wetting agent | 5 | 30 |

These fibers and fabrics can be used in different applications such as in wet wipes to achieve improved softness together with improved wettability and lotion management which are benefits for the end-users.

Another object of the invention is to provide a nonwoven layer as an acquisition/distribution layer which significantly reduces the inlet time and rewet value in combination with topsheets.

Surprisingly it has been found that the inlet time and rewet performance of topsheets is significantly improved when these topsheets are combined with a second layer of a thermobonded nonwoven fabric comprising man-made cellulosic fibers.

The inventive hygiene product comprises two layers of nonwoven fabric and is characterised in that the first layer comprises a synthetic fiber or hydrophobic man-made cellulosic fiber and the second layer comprises a man-made cellulosic fiber.

The first layer may consist of 100% of hydrophobic man-made cellulosic fiber or consist of blends of 75 to 99.5% by mass of hydrophobic man-made cellulosic fiber and 0.5 to 25% by mass of man-made cellulose fiber provided that the total amount is 100% by mass. The first layer can also be synthetic fibers like polyester.

In a preferred embodiment the second layer consists of a thermobonded nonwoven of man-made cellulosic fiber and a thermoplastic material, wherein the thermobonded nonwoven consists of 50 to 90% by mass of man-made cellulosic fibers and 50 to 10% by mass of thermoplastic fibers provided that the total amount is 100% by mass.

Appropriate for the thermobonded nonwoven are man-made cellulosic fibers with modified cross-sections, such as multilobal, irregular, triangular and hollow cross-sections.

A preferred man-made cellulosic fiber for the use in the thermobonded nonwoven is a trilobal man-made cellulosic fiber. Such a fiber is available from Lenzing AG under the trademark "Viscostar". The titer of this fiber is from 1.3 to 6.7 dtex, preferably 3 to 4 dtex. Another preferred man-made cellulosic fiber for the use in the thermobonded nonwoven is a lyocell fiber. The titer of the lyocell fiber is in the range of 0.9 to 9 dtex, preferably of 3.3. to 6.7 dtex. A lyocell fiber is available from Lenzing AG under the trademark "Tencel". The staple length of both fiber types is from 4 to 90 mm, preferably 10 to 60 mm.

The preferred thermoplastic fiber is a bicomponent fiber, for example a core-sheath PET/CoPET bicomponent fiber, a core-sheath PET/PE bicomponent fiber or a core-sheath-PE/PP bicomponent fiber.

The layer is an airlaid, drylaid or wetlaid nonwoven, which can be made by those respective processes. All bonding processes are possible. The nonwoven is a needle-punched, hydroentangled, thermal bonded or chemical bonded nonwoven.

A preferred nonwoven web is made by the "Lyocell melt-blown process" where the nonwoven web is directly produced by a melt-blowing process employing a cellulose solution in N-methyl-morpholine-N-oxide ("NMMO") as laid open in WO 2007/124522.

The nonwovens have a weight per unit area of between 5 to 100 $g/m^2$, preferably 10 to 40 $g/m^2$.

EXAMPLE 3

30 $g/m^2$ nonwoven fabrics were manufactured from different fiber types and their blends through thermal bonding processes (through air bond) for use in an acquisition/distribution layer (ADL).

Parallel-laid webs were made and the compressed webs were heated for 2 minutes at 150° C. to thermally bond the fabrics. The mean fabric area density was approximately 30 $g/m^2$. The thermal bonded ADL layers made and tested were:

A blend of 70% "Viscostar" trilobal viscose (3.3 dtex) and 30% bicomponent binder fiber (4 dtex, 50:50 concentric sheath-core polyethylene-polypropylene), used in samples 3.1, 3.3, 3.5 and 3.7.

A blend of 70% Tencel 3.3 dtex and 30% bicomponent binder fiber (4 dtex, 50:50 concentric sheath-core polyethylene-polypropylene), used in samples 3.6 and 3.8.

For these trials, 3 different apertured fabrics at 30 $g/m^2$ were used for topsheets. A typical absorbent core was used and ADL nonwoven fabrics (30 $g/m^2$) were placed between the topsheets and absorbent core. Inlet time and rewet was tested according to the test methods described below. The results of these trials are given in table 3.

Initial Testing of ADL Layers

The inlet-rewet test used to assess the ADL was a further modified version of the method outlined in US 2007/0219517. Samples of topsheet, ADL and core material were cut to size and weighed.

The components were laid on top of one another - with the topsheet uppermost, the ADL in the centre and the core at the bottom, then clamped in the test rig.

The inlet time was measured as before with 4.0 ml of standard test liquid pipetted onto the top sheet from a height of 3 cm. The time was recorded from the initial release of the liquid to the moment all the liquid passed through or into the top sheet.

The rewet was also measured as before, using a stack of ten 7 cm diameter Whatman 41 filter papers. However, after completion of the test the test sample was immediately disassembled and the three components were also weighed to calculate the distribution of the liquid through the sample. One test was performed with no ADL for comparison.

TABLE 3

| Sample | Top sheet (first layer) | ADL (second layer) | Inlet time (sec) | Rewet (%) |
|---|---|---|---|---|
| 3.1 | 90% Hydrophobic viscose + 10% Tencel (sample 1.4) | 70% Trilobal viscose 3.3 dtex + 30% bicomponent fibers (thermal bond) | 4.3 | 20 |
| 3.2 | 90% Hydrophobic viscose + 10% Tencel (sample 1.4) | no ADL (comparison) | 4.8 | 47 |
| 3.3 | Hydrophobic viscose (sample 1.5) | 70% Trilobal viscose 3.3 dtex + 30% bicomponent fibers (thermal bond) | 4.3 | <1.5 |
| 3.4 | Hydrophobic viscose (sample 1.5) | no ADL (comparison) | >20 | Not determinable |
| 3.5 | Hydrophobic viscose at 0.01% AKD | 70% Trilobal viscose 3.3 dtex + 30% bicomponent fibers (thermal bond) | 4.6 | 29 |
| 3.6 | Hydrophobic viscose (sample 1.5) | 70% Tencel 3.3 dtex + 30% bicomponent fibers (thermal bond) | 4.0 | <1.5 |
| 3.7 | Polyester | 70% Trilobal viscose 3.3 dtex + 30% bicomponent fibers (thermal bond) | 4.0 | <1.0 |
| 3.8 | Polyester | 70% Tencel 3.3 dtex + 30% bicomponent fibers (thermal bond) | 4.0 | <1.0 |

It can be seen that the nonwoven fabrics made of 70% trilobal viscose or 70% lyocell fibers (Tencel) in blends with 30% bicomponent fibers processed through carding and thermal bonding improves significantly the rewet performance of the absorbent pads if it is used as an acquisition/distribution layer in a combination with topsheets made of hydrophobic man-made cellulosic fibers and also with polyester topsheets (sample 3.7 and 3.8).

The inventive nonwoven fabrics are used in disposable hygiene products, like diapers, feminine pads and incontinence products. Hygiene products comprising one layer of a nonwoven fabric (a one layer nonwoven) which nonwoven fabric comprises a blend of man-made cellulosic fibers and hydrophobic man-made cellulosic fibers and which nonwoven is treated with a wetting agent are especially suited as wet wipes.

What is claimed is:

1. A hygiene product comprising at least one layer of a nonwoven wherein the at least one layer of the nonwoven comprises hydrophobic man-made cellulosic fibers, and wherein the layer or the layers has or have a rewet value of equal to or less than 30% and a liquid strike through time of equal to or less than 6 seconds.

2. The hygiene product according to claim 1, wherein the at least one layer of nonwoven fabric further comprises man-made cellulosic fibers and optionally a wetting agent.

3. The hygiene product according to claim 1 or 2, wherein the nonwoven fabric comprises a blend of 75 to 90% by mass of hydrophobic man-made cellulosic fibers and 25 to 10% by mass of man-made cellulosic fibers, provided that the total amount of the nonwoven fabric is 100% by mass.

4. The hygiene product according to claim 2, wherein the hydrophobic man-made cellulosic fibers are treated with a hydrophobic agent.

5. The hygiene product according to claim 4, wherein the hydrophobic agent is an alkyl ketene dimere.

6. The hygiene product according to claim 4 or 5, wherein the hydrophobic man-made cellulosic fibers contain the hydrophobic agent in an amount of 0.005 to 0.5% per mass.

7. The hygiene product according to claim 6, wherein the hydrophobic man-made cellulosic fibers contain the hydrophobic agent in an amount of 0.01 to 0.1% per mass.

8. The hygiene product according to claim 1 comprising two layers of nonwoven fabrics, wherein a first layer comprises hydrophobic man-made cellulosic fibers and a second layer comprises man-made cellulosic fibers.

9. The hygiene product according to claim 8, wherein the first layer is an airlaid, drylaid or wetlaid nonwoven.

10. The hygiene product according to claim 1, wherein the at least one layer is an airlaid, drylaid or wetlaid nonwoven.

11. The hygiene product according to claim 1, wherein the nonwoven is selected from the group consisting of a needle-punched, hydroentangled, thermal bonded or chemical bonded nonwoven or nonwoven web directly produced by a melt-blowing process employing a cellulose solution in N-methyl-morpholine-N-oxide ("NMMO").

12. The hygiene product according to claim 1, wherein the hygiene product is a disposable hygiene product.

13. The hygiene product according to claim 1, wherein the hygiene product is a wet wipe.

14. The hygiene product according to claim 12, wherein the disposable hygiene product is selected from the group consisting of diapers, feminine pads and incontinence products.

15. The hygiene product according to claim 13, wherein the wet wipe is selected from the group consisting of toilet wipes, facial wipes, cosmetic wipes, baby wipes and sanitary wipes for cleaning and disinfection.

16. The hygiene product according to claim 8, wherein the first layer consists of 100% of hydrophobic man-made cellulosic fibers.

17. The hygiene product according to claim 8, wherein the first layer consists of a blend of 75 to 99.5% by mass of hydrophobic man-made cellulosic fibers and 0.5 to 25% by mass of man-made cellulose fibers provided that the total amount is 100% by mass.

18. The hygiene product according to claim 8, wherein the second layer consists of a thermobonded nonwoven of man-made cellulosic fiber and a thermoplastic material.

19. The hygiene product according to claim 18, wherein the thermobonded nonwoven consist of 50 to 90% by mass of man-made cellulosic fibers and 50 to 10% by mass of thermoplastic fibers provided that the total amount is 100% by mass.

20. The hygiene product according to claim 18 or 19, wherein the man-made cellulosic fiber has a modified cross-section, such as multilobal, irregular, triangular and hollow, preferred a trilobal man-made cellulosic fiber.

21. The hygiene product according to claim 18 or 19, wherein the man-made cellulosic fiber is a lyocell fiber.

22. The hygiene product according to claim 18 or 19, wherein the thermoplastic fiber, is a bicomponent fiber.

* * * * *

UNITED STATES PATENT AND TRADEMARK OFFICE
CERTIFICATE OF CORRECTION

PATENT NO. : 11,083,817 B2
APPLICATION NO. : 14/381029
DATED : August 10, 2021
INVENTOR(S) : Shayda Rahbaran et al.

It is certified that error appears in the above-identified patent and that said Letters Patent is hereby corrected as shown below:

In the Claims

Column 7:
Claim 3, Lines 3-4, "25 to 10%" should read --10 to 25%--.

Column 8:
Claim 17, Line 4, "cellulose" should read --cellulosic--;
Claim 19, Line 3, "50 to 10%" should read --10 to 50%--;
Claim 20, Lines 3-4, "section, such as multilobal, irregular, triangular and hollow, preferred a trilobal man-made cellulosic fiber" should read --section, including multilobal, irregular, triangular and hollow cross-sections, optionally a trilobal cross-section--;
Claim 22, Line 2, "fiber," should read --fiber--.

Signed and Sealed this
Nineteenth Day of September, 2023

Katherine Kelly Vidal
*Director of the United States Patent and Trademark Office*